United States Patent
Lateef et al.

(10) Patent No.: US 10,269,447 B2
(45) Date of Patent: Apr. 23, 2019

(54) ALGORITHM, DATA PIPELINE, AND METHOD TO DETECT INACCURACIES IN COMORBIDITY DOCUMENTATION

(71) Applicant: OPPORTUNE ACQUISTION, LLC, Houston, TX (US)

(72) Inventors: Omar Lateef, Hinsdale, IL (US); Bala Hota, Hinsdale, IL (US)

(73) Assignee: OPPORTUNE ACQUISITION, LLC, Houston, TX (US)

( * ) Notice: Subject to any disclaimer, the term of this patent is extended or adjusted under 35 U.S.C. 154(b) by 0 days.

(21) Appl. No.: 15/478,007

(22) Filed: Apr. 3, 2017

(65) Prior Publication Data

US 2018/0039738 A1    Feb. 8, 2018

Related U.S. Application Data

(60) Provisional application No. 62/371,466, filed on Aug. 5, 2016, provisional application No. 62/416,388, filed on Nov. 2, 2016.

(51) Int. Cl.
*G06F 19/00* (2018.01)
*G16H 10/60* (2018.01)
(Continued)

(52) U.S. Cl.
CPC ......... *G16H 10/60* (2018.01); *G06F 16/2282* (2019.01); *G06F 16/23* (2019.01); *G16H 50/70* (2018.01)

(58) Field of Classification Search
CPC ............... G06Q 50/22; G06Q 10/06
(Continued)

(56) References Cited

U.S. PATENT DOCUMENTS

| | | | | |
|---|---|---|---|---|
| 5,404,292 A | * | 4/1995 | Hendrickson | ......... G06F 19/327 128/920 |
| 2002/0173988 A1 | * | 11/2002 | Dang | ................... G06F 19/328 705/2 |

(Continued)

OTHER PUBLICATIONS

International Search Report and Written Opinion dated May 30, 2017 in PCT Application No. PCT/US2017/032229.

*Primary Examiner* — Hiep V Nguyen
*Assistant Examiner* — Trang T Nguyen
(74) *Attorney, Agent, or Firm* — Bracewell LLP; Brad Y. Chin; Karthika Perumal

(57) ABSTRACT

Systems and methods for detecting inaccuracies in comorbidity documentation are provided. An example method can include retrieving patient data from a hospital records database, generating a first data structure representing a list of patient identifiers, retrieving patient symptom data for each patient identifier listed in the first data structure, generating, a second data structure by assigning the retrieved patient symptom data to the eligible patients represented in the first data structure, retrieving, a plurality of lookup tables, generating a third data structure by applying the lookup tables to the second data structure to assign a CC or a MCC value to at least one unique patient identifier of the second data structure, and storing the third data structure to the memory. In some implementations, the method can include updating the hospital records database with the CC or the MCC value assigned to the at least one unique patient.

20 Claims, 10 Drawing Sheets

(51) Int. Cl.
*G06F 16/23* (2019.01)
*G06F 16/22* (2019.01)
*G16H 50/70* (2018.01)

(58) Field of Classification Search
USPC ........................................................ 705/2, 3
See application file for complete search history.

(56) References Cited

U.S. PATENT DOCUMENTS

| | | | |
|---|---|---|---|
| 2009/0099869 A1* | 4/2009 | Darin | G06F 19/328 |
| | | | 705/3 |
| 2010/0082363 A1* | 4/2010 | Warner | G06Q 50/22 |
| | | | 705/2 |
| 2010/0204920 A1* | 8/2010 | Dranitsaris | G06F 19/3431 |
| | | | 702/19 |
| 2015/0088548 A1* | 3/2015 | Charlot | G06F 19/322 |
| | | | 705/3 |
| 2015/0127375 A1* | 5/2015 | Hwang | G06Q 50/24 |
| | | | 705/3 |
| 2016/0089356 A1* | 3/2016 | Dalton | C07C 255/60 |
| | | | 514/522 |
| 2016/0259916 A1* | 9/2016 | Putnam | G06F 19/328 |

* cited by examiner

| 805 | |
|---|---|
| 815a | 810a |
| 815b | 810b |
| 815c | 810c |
| ... | ... |
| 815x | 810x |

800

| 855a | 855b | 855c | | 860a |
|---|---|---|---|---|
| 865a | 870a | 875a | | 860b |
| 865b | 870b | 875b | | 860c |
| 865c | 870c | 875c | | ... |
| ... | ... | ... | | 860x |
| 865x | 870x | 875x | | 860y |
| 865y | 870y | 875y | | 860z |
| 865z | 870z | 875z | | |
| ... | ... | ... | | |

ALGORITHM, DATA PIPELINE, AND METHOD TO DETECT INACCURACIES IN COMORBIDITY DOCUMENTATION

RELATED APPLICATIONS

The present application claims the benefit of U.S. Provisional Patent Application No. 62/371,466, titled "ALGORITHM, DATA PIPELINE, AND METHOD TO DETECT INACCURACIES IN COMORBIDITY DOCUMENTATION," and filed on Aug. 5, 2016, and U.S. Provisional Patent Application No. 62/416,388, titled "ALGORITHM, DATA PIPELINE, AND METHOD TO DETECT INACCURACIES IN COMORBIDITY DOCUMENTATION," and filed on Nov. 2, 2016, the entire contents of which are hereby incorporated by reference.

BACKGROUND

Technological advances in medical record keeping have led to a fragmentation of medical records systems. For example, the transition from paper files to electronic records has resulted in the records for a single hospital visit or admission by a single patient being divided up among several separate and distinct databases. Records of the hospital visit may include physician notes, hospital billing information, clinical test results, and pharmacy records, with each subset of the records stored separately. Different data formats, interfaces, and security measures as required by the Health Insurance Portability and Accountability Act (HIPAA) can make it impractical or impossible to generate a consolidated view of all historical patient data. Furthermore, a patient's medical history may include multiple visits or admissions to multiple different healthcare providers. Some data or data sources may be hidden such that they remain inaccessible unless specifically sought out. Modern electronic medical record keeping has thus created technological barriers to access to and visibility of a patient's full medical history.

SUMMARY

This disclosure generally relates to systems and methods for detecting inaccuracies in comorbidity documentation. At least one aspect is directed to a system for detecting inaccuracies in comorbidity documentation. The system can include a memory and a processor. The memory and processor can be configured to retrieve patient data from a hospital records database, generate a first data structure representing a list of patient identifiers. Each patient identifier can correspond to an eligible patient who was admitted to a hospital for in-patient care during a specified time period. The memory and processor can be configured to retrieve patient symptom data for each patient identifier listed in the first data structure from one or more of a professional records database, a hospital records database, or a clinical records database. The memory and processor can be configured to generate a second data structure by assigning the retrieved patient symptom data to the eligible patients represented in the first data structure. The memory and processor can be configured to retrieve, from the memory, a plurality of lookup tables. The plurality of lookup tables can comprise a first table comprising diagnostic codes assigned to chronic condition categories, a second table comprising a list of clinical discrete data corresponding to unambiguous indicators of each chronic condition, and a third table comprising diagnostic codes assigned to complication or comorbidity (CC) or major complication or comorbidity (MCC) values for each chronic condition category. The memory and processor can be configured to generate a third data structure by applying the lookup tables to the second data structure to assign a CC or a MCC value to at least one unique patient identifier of the second data structure, and store the third data structure to the memory.

At least one aspect is directed to a method of detecting inaccuracies in comorbidity documentation. The method can include retrieving, by the data processing system, patient data from a hospital records database. The method can include generating, by the processor, a first data structure representing a list of patient identifiers, each corresponding to an eligible patient having a through hospitalization for a specified time period. The method can include retrieving patient symptom data for each patient identifier listed in the first data structure from one or more of a professional records database, a hospital records database, or a clinical records database. The method can include generating, by the processor, a second data structure by assigning the retrieved patient symptom data to the eligible patients represented in the first data structure. The method can include retrieving, from the memory. The plurality of lookup tables can comprise a first table comprising diagnostic codes assigned to chronic condition categories, a second table comprising a list of clinical discrete data corresponding to unambiguous indicators of each chronic condition, and a third table, comprising diagnostic codes assigned to complication or comorbidity (CC) or major complication or comorbidity (MCC) values for each chronic condition category. The method can include generating, by the processor, a third data structure by applying the lookup tables to the second data structure to assign a CC or a MCC value to at least one unique patient identifier of the second data structure. The method can include storing the third data structure to the memory.

These and other aspects and embodiments are discussed in detail below.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 8 is an illustration of an example vector and an example data structure for use in detecting inaccuracies in comorbidity documentation, according to another illustrative implementation;

DETAILED DESCRIPTION

Figure 1:
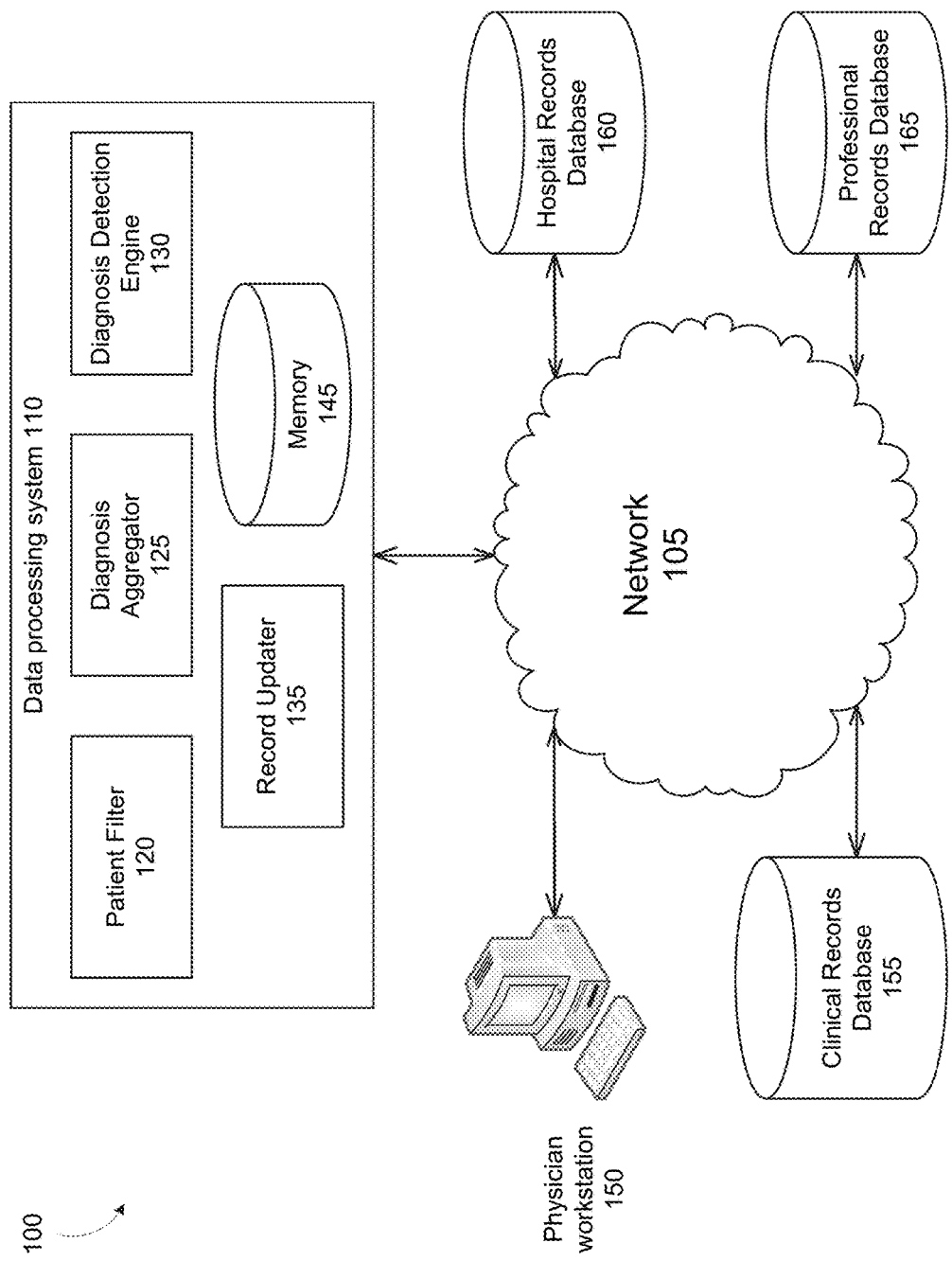
FIG. 1 is a block diagram illustrating an example environment for detecting inaccuracies in comorbidity documentation, according to an illustrative implementation.

This disclosure relates to a system for addressing the fragmentation of medical records among multiple electronic medical record systems. The systems add a new analysis and detection layer to electronic medical records systems that can aid in detecting inaccuracies in comorbidity documentation that may be caused in part by this data fragmentation. For example, hospitals and other institutional providers of medical care can use diagnosis-related groups (DRGs) to classify and record diagnoses of patients and treatments given. The DRG for a patient may include a code for a chronic condition. The code can include a complication or comorbidity (CC) or a major complication or comorbidity (MCC) designation. In some cases, however, data fragmentation may cause a physician or other care provider to fail to record a CC or MCC when recording a DRG for a patient who is unambiguously afflicted with a chronic condition justifying a CC or MCC designation. Failure to record CCs or MCCs can lead to problems for both patients and healthcare providers. First, absence of an applicable CC or MCC designation may lead to an inaccurate assessment of the patient's overall health risk. For example, a patient with a chronic condition seeking medical attention for an ailment unrelated to the chronic condition may receive treatment that fails to account for the additional health risk caused by the chronic condition. Second, failure to record or account for a chronic condition can skew benchmarking of patient outcomes. For example, hospitals are ranked on patient outcomes, but the rankings are adjusted based on patient risk; i.e., a hospital that achieves similar overall outcomes when treating higher risk patients will achieve a higher rank. Without proper accounting for chronic conditions, a hospital may receive a lower rank that justified by the aggregate health risk of its patient pool. Third, payers for medical care (e.g., HMOs, insurance companies, Medicare, and Medicaid) may reimburse at a higher rate for treatment of individuals with chronic conditions. Thus, failure to record chronic conditions in all patient records may result in the healthcare provider receiving a lower reimbursement for services rendered than it is entitled to. In sum, the system can help ensure that patients with the highest health risk receive appropriate care, that hospital mortality rates accurately reflect the aggregate health risk of its patient pool, and that the hospital can properly account for all healthcare services provided to patients with chronic conditions.

The system can thus improve the accuracy and effectiveness of hospital electronic medical records infrastructure. The system can maintain consistency in the recordation of chronic conditions across various electronic medical records systems to ensure that each electronic medical records system accurately reflects complete and up-to-date patient health risk data. This can increase the effectiveness of the electronic medical records systems in allowing physicians to determine appropriate treatment for each patient, and hospitals to perform proper benchmarking and accounting of services rendered.

The systems and methods described herein can evaluate electronic medical records to determine the presence of comorbidities and complications. The system can execute an algorithm and data pipeline that extracts data from electronic records to identify combinations of symptoms indicative of chronic and acute conditions. For example, it can compare coded diagnoses found in hospital records—data used for Centers for Medicare & Medicaid Services (CMS) quality measures for inpatients—with potential diagnoses as derived from alternate sources of information. The alternate sources of data for detecting conditions can include professional records data, historical hospital records data, and clinical records data from current and prior encounters. The system can identify the potential presence of diagnosis for patients including, without limitation:

Cancer
Major depression
Epilepsy
High cholesterol
Obesity
Malnutrition
Hypertension
Chronic kidney disease
Congestive heart failure
Ischemic Heart Disease
Osteoporosis
Chronic Obstructive Pulmonary Disease
Osteoarthritis
Dementia
Cerebrovascular Disease
Asthma
Bipolar Disorder
Diabetes mellitus
Hyponatremia
Hypernatremia
Acute Renal Failure The system can use data from different sources to perform a diagnosis. For example, the system can use professional diagnosis data and prior hospital records data for at least the conditions in the following set: {Cancer, Major depression, Epilepsy, Ischemic Heart Disease, Osteoporosis, Chronic Obstructive Pulmonary Disease, Osteoarthritis, Dementia, Cerebrovascular Disease, Asthma, and Bipolar Disorder}. For the conditions in the following set, the system can use, without limitation, professional diagnosis data, prior hospital records data, and clinical records data: {High cholesterol, Obesity, Malnutrition, Hypertension, Chronic Kidney Disease, Congestive Heart Failure, Diabetes Mellitus, Hyponatremia, Hypernatremia, and Acute Renal Failure}. The system can receive and analyze data including, but not limited to, body mass index, vital sign data such as blood pressure, clinical lab values such as cholesterol, and medication data where applicable.

Following detection of possible conditions, the most likely diagnosis applicable to the current admission can be imputed via the algorithm based on a combination of factors: time of diagnoses, severity of diagnoses, acuity of diagnoses from professional diagnosis and prior hospital records diagnosis data sets, and when clinical records data are used, degree of abnormality of these data. This diagnosis can then be judged to be a complication or comorbidity (CC) or major complication or comorbidity (MCC) based on published criteria established by a payer for medical services (such as Medicare, the National Health Service, etc.) for inclusion or exclusion in CC/MCC groups. The resulting diagnosis code and CC/MCC designation can be useful for integration into a new calculation of a Diagnosis-Related Group (DRG) as well as a recalculation of benchmarked quality score based on current payer guidance. The algorithm can be combined with a data pipeline. This pipeline is a methodology for data extraction to create the requisite data model, as well as an output data set useful for analytic purposes (e.g. calculation of new DRG values, visualization of rates of potential missed diagnoses).

The algorithm and data pipeline have direct applicability in a number of domains. First, the algorithm and data pipeline can facilitate quality improvement initiatives. The algorithm can aid in the identification of inefficiencies in existing workflow and documentation that can lead to unfavorable case mix measurement, which can adversely affect expected outcomes for quality metrics. The identification of cases in which comorbidity documentation and coded hospital diagnoses is potentially incorrect can be used as a benchmarking tool, an audit tool, and a method to focus clinical documentation improvement initiatives. Second, the algorithm and data pipeline can improve comorbidity capture in DRG coding. Finally, the algorithm and data pipeline can serve as tools to measure clinician documentation quality, by enabling analytics that quantify error rates in clinical note completeness, and associated coding of diagnoses.

The algorithm and data pipeline, by using clinical records data within the electronic record, is a new method of detecting diagnoses present in patients. Because the clinical records data used are objective criteria that unambiguously define diagnoses, the algorithm can detect cases where diagnoses are inappropriately missing from clinical documentation. The algorithm can exploit the fact that even if clinical records data that demonstrate a diagnosis is present exist, unless a diagnosis is captured in a clinician note (especially the discharge summary), it will not be coded as a diagnosis for the encounter by medical coders. The algorithm, using objective clinical records data, can detect signals indicating a diagnosis and find relevant records.

The algorithm and data pipeline are implemented in a new system that connects the various separate databases housing electronic medical records in an unconventional manner. The system generates a transient data structure representing an amalgamation of electronic medical records retrieved from the various sources, and simplified for easier application of rules. The system can provide an analysis and detection layer over and above existing hospital IT infrastructure that allows for the application of the rules on the transient data structure. Electronic medical data can be pulled and subjected to rule-based analysis on demand. Each rule can exist as an object or class in JavaScript, TypeScript or the like. Each condition can have its own object. Rules can therefore be extensible, with each new rule created as a new object. The rules can, for example, flag when electronic medical records evidence the unambiguous presence of a chronic condition that has not been recorded in an electronic medical record. The system can provide a notification to the healthcare provider that the chronic condition is present. In some implementations, the system can notify the healthcare provider in real time via secure electronic message. In some implementations, the system can leave a message, notice, or flag in the patient's electronic medical records for the healthcare provider to address the next the electronic medical record is accessed.

FIG. 1 is a block diagram illustrating an example environment 100 for detecting inaccuracies in comorbidity documentation. The environment 100 can include a data processing system 110, a physician workstation 150, a clinical records database 155, a hospital records database 160, and a professional records database 165, all communicatively connected via a computer network 105.

The physician workstation 150 can include a PC or PC-type computer used by a physician or healthcare worker to retrieve and enter healthcare data for a patient. The physician workstation 150 can connect to the clinical records database 155 via a secure, private computer network such as an internal hospital local area network (LAN) or via a wider, unsecure computer network 105 such as the Internet. During a patient visit, the healthcare worker can retrieve a patient's medical record to the physician workstation 150 from the clinical records database 155. The healthcare worker can enter new medical information concerning the patient into the patient's medical record, and transmit it back to the clinical records database 155.

The clinical records database 155 can store encounter-level diagnoses of the patient in prose or in the form of diagnostic codes, such as those that conform to diagnosis-related groups (DRG). The clinical records database 155 can additionally include medical data such as the results of tests, screens, or imaging; for example, and without limitation, blood tests, urine screens, biopsies, X-rays, ultrasounds, or MRI images. The clinical records database 155 can store the patient's medical records, and make them available for future visits by the patient to the same or different medical facility.

The hospital records database 160 can include records of all technical resources provided by the hospital. Such services can include emergency room visits and outpatient surgeries, including anesthesia and medications administered. The hospital records database 160 can store billing records for hospital services.

The professional records database 165 can include records of all services performed by physicians, specialists, and other healthcare workers. The professional records database 165 can store billing records for physician services. Billing for physician services can be separate from billing for hospital services such as visits to the ER or other treatment centers. Professional services can include doctor's office visits, lab tests or medical imaging performed, and physician-related services such as review of X-rays, MRIs, or lab tests.

The data processing system 110 can perform the operations for detecting comorbidity in patient data. The data processing system 110 can include a patient filter 120, a diagnosis aggregator 125, a diagnosis detection engine 130, a records updater 135, and a memory 145. The data processing system 110 can retrieve data from the clinical records database 155, the hospital records database 160, and the professional records database 165 via the network 105.

The patient filter 120 can be configured to retrieve patient data from the hospital records database 160, and generate the first data structure. The first data structure can take the form of a table, array, matrix, or database such as a relational database.

The first data structure can represent a list of patient identifiers. Each patient identifier can correspond to an eligible patient having a through hospitalization for a specified time period; that is, a patient admitted to in-patient care at a hospital. The patient filter 120 can generate the first data structure by taking a list of all patients retrieved from the hospital records database 160 over a certain predetermined time period, and filtering out the patients who were not admitted. There may not be an indicator, flag, or data point in the patient data that indicates whether or not a patient was admitted. The patient filter 120 must therefore determine whether each patient was admitted based on other information in the patient data. For example, the patient filter 120 can determine whether a patient was admitted based on encounter-level data such as encounter type and encounter location. This process is discussed in more detail below with regard to FIG. 5. The first data structure can represent a list of patient identifiers corresponding to an eligible patient having a through hospitalization for a specified time period. The patient filter 120 can store the first data structure in the memory 145.

The diagnosis aggregator 125 can be configured to retrieve patient symptom data corresponding to each patient identifier listed in the first data structure. The patient symptom data can include data regarding both symptoms observed or measured, and can additionally include diagnoses related to observed or measured symptoms. The patient symptom data can take the form of codes such as DRGs. The diagnosis aggregator 125 can be configured to retrieve patient symptom data from the professional records database 165, the hospital records database 160, and/or the clinical records database 155. The diagnosis aggregator 125 can retrieve all patient symptom data for a predetermined period of time up to and including the current admission. The diagnosis aggregator 125 can use the retrieved patient symptom data to generate a second data structure. The diagnosis aggregator 125 can generate the second data structure by assigning the retrieved patient symptom data to the eligible patients represented in the first data structure. The second data structure can include all patient symptom data for the eligible patients for a predetermined period of time up to and including the current admission. The second data structure can include an attribute column indicated whether each patient symptom in the patient symptom data was retrieved from the professional records database, the hospital records database, or the clinical records database. The second data structure can take the form of a table, array, matrix, or database such as a relational database. The diagnosis aggregator 125 can store the second data structure in the memory 145.

The diagnosis detection engine 130 can be configured to assign complication or comorbidity (CC) or major complication or comorbidity (MCC) values to one or more of the patient identifiers in the second data structure. The diagnosis engine 130 can analyze the patient symptom data in the second data structure and determine the presence of any undiagnosed or unrecorded CC or MCCs. The diagnosis engine 130 can analyze the patient symptom data by applying a set of lookup tables to the values in the second data structure. The diagnosis engine 130 can do so by retrieving, from the memory 145, a plurality of lookup tables. The lookup tables are described in more detail below with regard to FIG. 2. The diagnosis engine can generate the third data structure by applying the lookup tables to the second data structure to assign a CC or a MCC value to at least one unique patient identifier of the second data structure. The diagnosis engine 130 can store the third data structure in the memory 145. In some implementations, the third data structure can take the form of an entity attribute table comprising columns for unique patient identifiers, conditions, CC or an MCC values, and classifications of whether each condition was present in one or more of the professional records database, the hospital records database, or the clinical records database.

The records updater 135 can be configured to update patient records to reflect any CC and MCC values assigned based on the analysis of the patient symptom data in the second data structure. In some implementations, the records updater 135 can update the hospital records database with the CC or the MCC value assigned to one or more patient identifiers.

Figure 2:
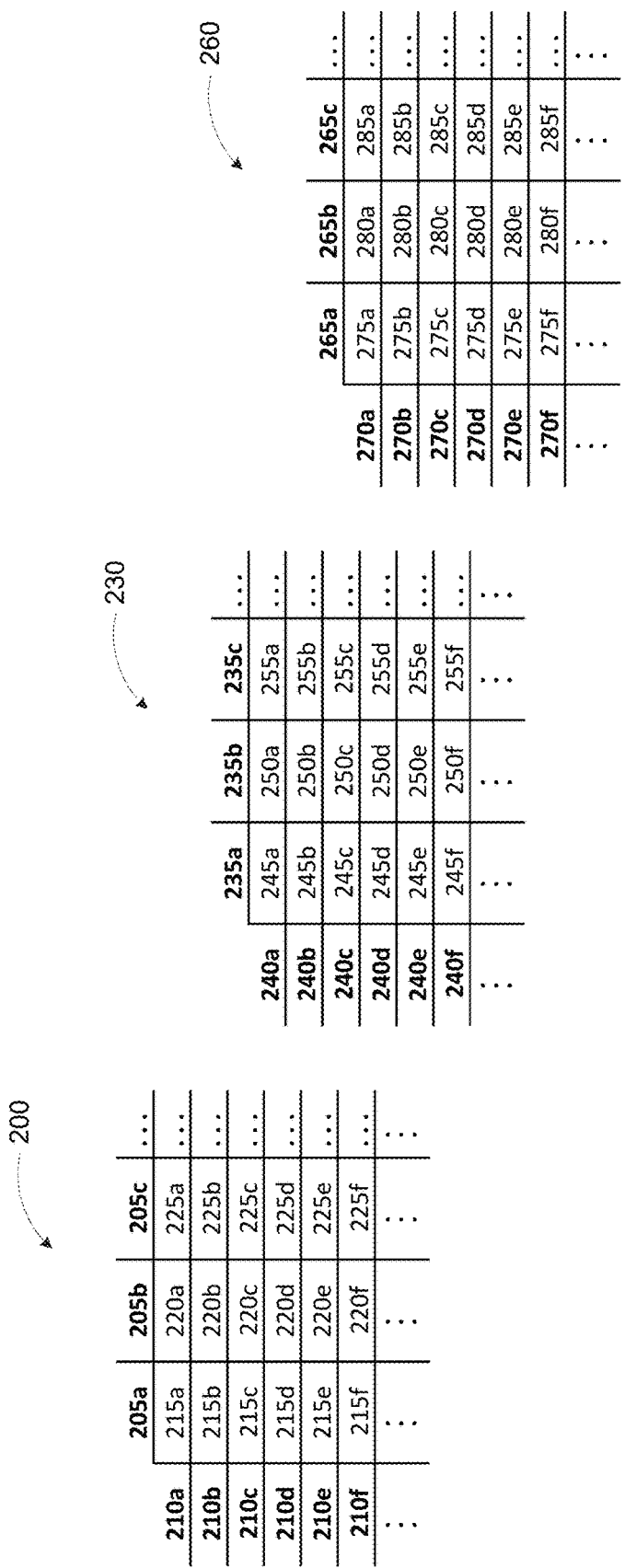
FIG. 2 is an illustration of example lookup tables for use in detecting inaccuracies in comorbidity documentation, according to an illustrative implementation.

FIG. 2 is an illustration of example lookup tables 200, 230, and 260 for use in detecting inaccuracies in comorbidity documentation. The first lookup table 200 can comprise diagnostic codes assigned to chronic condition categories. The second lookup table 230 can comprise a list of clinical discrete data corresponding to unambiguous indicators of each chronic condition. The third lookup table 260 can comprise diagnostic codes assigned to complication or comorbidity (CC) or major complication or comorbidity (MCC) values for each chronic condition category. The diagnosis detection engine 130 can use the lookup tables to generate a data structure linking a CC or MCC code with a patient identifier.

The first lookup table 200 can comprise diagnostic codes assigned to chronic condition categories. The diagnostic codes can comprise ICD-9 and ICD-10 codes. The chronic condition categories can include, without limitation, cancer, major depression, epilepsy, ischemic heart disease, osteoporosis, chronic obstructive pulmonary disease, osteoarthritis, dementia, cerebrovascular disease, asthma, bipolar disorder, high cholesterol, obesity, malnutrition, hypertension, chronic kidney disease, congestive heart failure, diabetes mellitus, hyponatremia, hypernatremia, and acute renal failure. In some implementations, each row 210 of the first lookup table 200 can correlate diagnostic codes with a chronic condition. Each column 205 can be a diagnostic code, a chronic condition, or other data. For example, 215a could be a chronic condition of hypertension, cell 220a could be an ICD-9 code related to hypertension, and cell 225a could be an ICD-10 code related to hypertension. The first lookup table 200 could have more or fewer columns as appropriate for a particular application. In some implementations, the rows 210 can represent chronic condition categories, where each chronic condition category can correspond to multiple chronic conditions. For example, the chronic condition of obesity could include obesity due to excess calories, obesity with alveolar hypoventilation, obesity complicating pregnancy, etc. In such implementations, each row 210 corresponding to a chronic condition category can include cells having diagnostic codes for each chronic condition within that category.

The second lookup table 230 can comprise a list of clinical discrete data corresponding to unambiguous indicators of each chronic condition. The list of clinical discrete data can include one or more of lab results, vital signs, or medication data that unambiguously indicate the presence of a medical diagnosis. For example, a blood pressure above a certain threshold can unambiguously indicate hypertension, an LDL counts above a certain threshold can unambiguously indicate high cholesterol, etc. In some implementations, each row 240 of the second lookup table 230 can correlate a type and value of clinical discrete data with a chronic condition or a chronic condition category. The columns 235 can represent the chronic condition or chronic condition category, and corresponding indicators from the clinical discrete data, respectively. In some cases, a chronic condition may have multiple indicators. For example, high cholesterol can be indicated by both clinical data including an elevated LDL measurement, and a hospital record including a prescription for a statin.

The third lookup table 260 can comprise diagnostic codes assigned to complication or comorbidity (CC) or major complication or comorbidity (MCC) values for each chronic condition category. The CC or MCC values can be diagnostic codes, such as ICD-9 and ICD-10 codes. In some implementations, each row 270 of the third lookup table 260 can correlate a chronic condition category with a CC or MCC value. The columns 265 can represent the chronic condition category, and one or more CC or MCC diagnostic codes corresponding to the chronic condition category.

Figure 3:
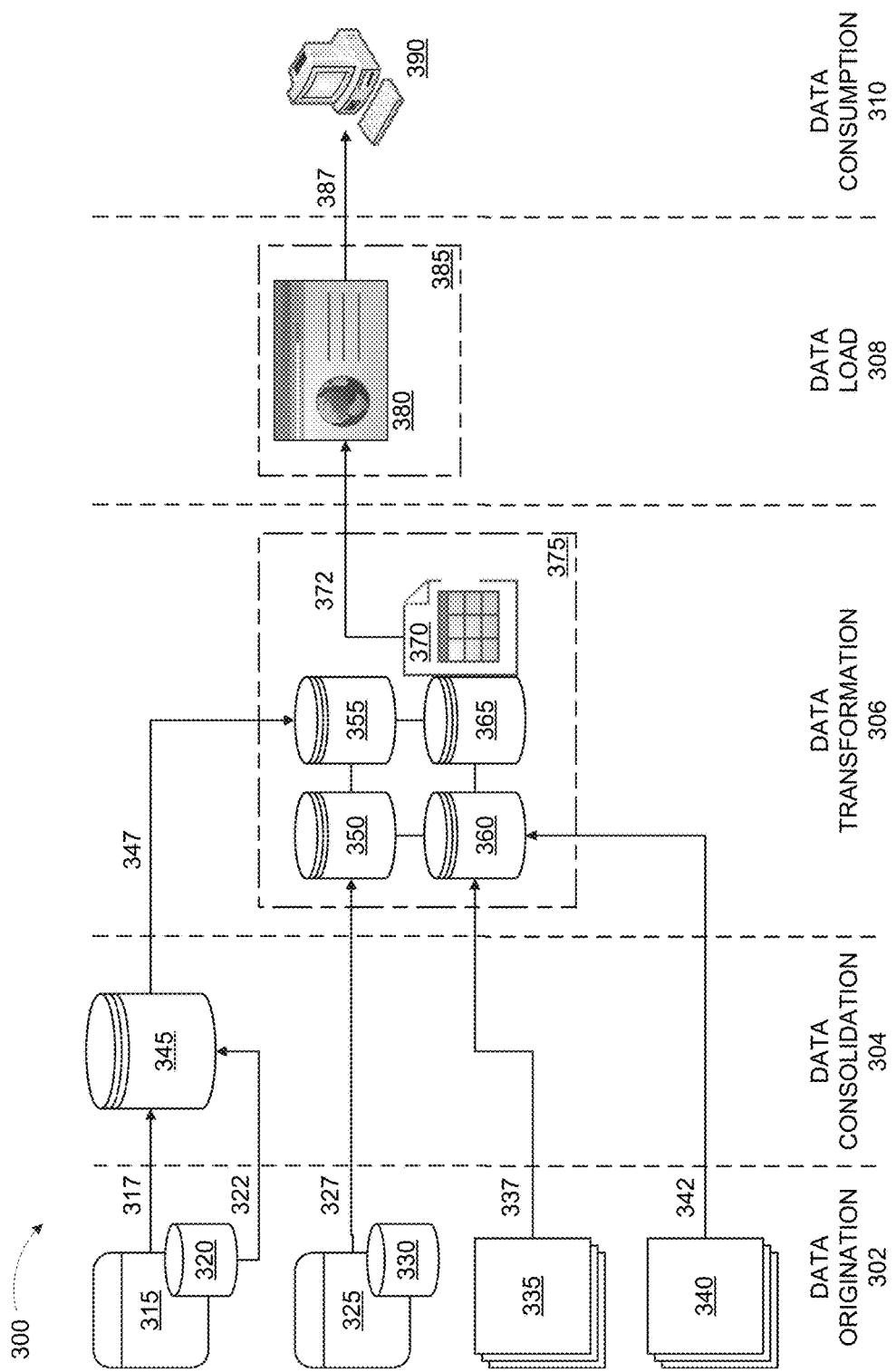
FIG. 3 is a block diagram illustrating an example logical data flow model for detecting inaccuracies in comorbidity documentation, according to an illustrative implementation.

FIG. 3 is a block diagram illustrating an example logical data flow model 300 for detecting inaccuracies in comorbidity documentation, according to an illustrative implementation. The model 300 includes 5 stages: a data origination stage 302, a data consolidation stage 304, a data transformation stage 306, a data load stage 308, and a data consumption stage 310.

The data original stage 302 includes an electronic medical records system 315 with an operational data store 320, an echocardiography system 325 with a reporting server 330, a DRG code data structure 335, and a patient mortality rate data structure 340. In some implementations, the medical records system 315 can include, for example and without limitation, the clinical records database 155, the hospital records database 160, and/or the professional records database 165, previously described. In some implementations, the respective databases may be combined or divided differently. The echocardiography system 325 can include results from echocardiograms performed on patients. In some implementations, the echocardiogram data can be alternatively stored in the clinical records database 155. In some implementations, the DRG code data structure 315 can include the first table 200 comprising diagnostic codes assigned to chronic condition categories. In some implementations, the DRG code data structure 315 can additionally include the third table 260 comprising diagnostic codes assigned to complication or comorbidity (CC) or major complication or comorbidity (MCC) values for each chronic condition category. In some implementations, the patient mortality rate data structure 340 can include mortality rates as provided by Medicare and as applied by Medicare for risk adjustment.

The data consolidation stage 304 includes a data warehouse 345. The data warehouse 345 receives patient medical record numbers 317 from the electronic medical records system 315. A script can extract patient medical record numbers 317 from the electronic medical records system 315 for mapping to patient keys in the data warehouse 345. The script can be of a TypeScript, JavaScript, or Node.js variant. The data warehouse 345 also receives patient medical data 322 from the operational data store 320. A script can extract, transform, and load the patient medical data 322 from the operational data store 320 into the data warehouse 345. The data transformations can generally re-architecture the various data formats into a single usable format. Following loading, the data warehouse 345 can contain data received from the clinical records database 155, the hospital records database 160, and/or the professional records database 165.

The data transformation stage 306 includes a private or public cloud service 375. In some implementations, the cloud service 375 can include the data processing system 110 previously described. In some implementations, the cloud service 375 can operate locally at a hospital or other medical facility. In some implementations, the cloud service 375 can operate remotely at a cloud service provider. The cloud service 375 can include one or more server systems executing one or more databases. The databases can include a cardiology database 350, a reporting database 355, a research database 360, and clinical data model database 365.

The clinical data model database 365 stores the clinical data model 370. The cardiology database 350 receives cardiology data 327 from the echocardiography system 325. A scrip can extract, transform, and load the cardiology data 327 from the echocardiography system 325 to the cardiology database 350. The reporting database 355 receives select table data 347 from the data warehouse 345. A script can extract, transform, and load the select table data 347 from the data warehouse 345 to the reporting database 355. The research database 360 receives DRG codes 337 from the DRG code data structure 335, and patient mortality rates 342 from the patient mortality rate data structure 340. In some implementations, the DRG codes 337 and the patient mortality rates 342 can be manually uploaded to the research database 360. In some implementations, a script can upload the DRG codes 337 and the patient mortality rates 342 to the research database 360. The cloud service 375 can combine the data from the cardiology database 350, the reporting database 355, and the research database 360 to generate the clinical data model 370. The cloud service 375 can store the clinical data model 370 in the clinical data model database 365. The clinical data model 370 can be a transient data structure that represents a simplified representation of the data that facilitates the application of rules and interoperability with other systems. For example, the cloud service 375 can share and store data using Fast Healthcare Interoperability Resources (FHIR). FHIR describes standard formats for the exchange of electronic medical records. Using FHIR, the cloud service 375 can share electronic medical records with other hospitals and non-hospital sources such as Medicare, Social Security, and pharmacies. In addition, the cloud service 375 can provide for the application of rules. The cloud service 375 can provide an analysis and detection layer that allows for the application of the rules on the clinical data model 370. Electronic medical data can be pulled and subjected to rule-based analysis on demand. Each rule can exist as an object or class in JavaScript, TypeScript or the like. Each condition can have its own object. Rules can therefore be extensible, with each new rule created as a new object. The rules can, for example, flag when electronic medical records evidence the unambiguous presence of a chronic condition that has not been recorded in an electronic medical record. The system can provide a notification to the healthcare provider that the chronic condition is present. In some implementations, the system can notify the healthcare provider in real time via secure electronic message. In some implementations, the system can leave a message, notice, or flag in the patient's electronic medical records for the healthcare provider to address the next time the electronic medical record is accessed.

The data load stage 308 includes a web application 380 executing on one or more application servers 385. The web application 380 can receive clinical data model data 372 from the clinical data model 370. The clinical data model data 372 can be transmitted from the cloud service 375 to the application server 385 via a secure database connection. The web application 380 can provide a user interface for execution on a client machine 390.

The data consumption stage 310 includes a user interface executing on the client machine 390. In some implementations, the client machine 390 can include the physician workstation 150 previously described. The client machine 390 can receive data 387 from the web application 380. The data 387 can include notifications and responses to user queries. The web application 380 can allow a healthcare provider to view the patient medical records retrieved from various sources in a single user interface. The healthcare provider can use the web application 380 to query patient medical records in the clinical data model 370. The web application 380 can notify the healthcare provider if a chronic condition should be included in the notes for the patient visit. The web application 380 can issue notifications in the form of messages in the electronic medical records or through direct secure email. The web application 380 can notify the healthcare provider about possibilities for additional care. The web application 380 can suggest a CC or MCC code to include in the notes. The healthcare provider can receive the notifications in real time while the healthcare provider has the patient's medical records open and make any suggested adjustments.

Figure 4:
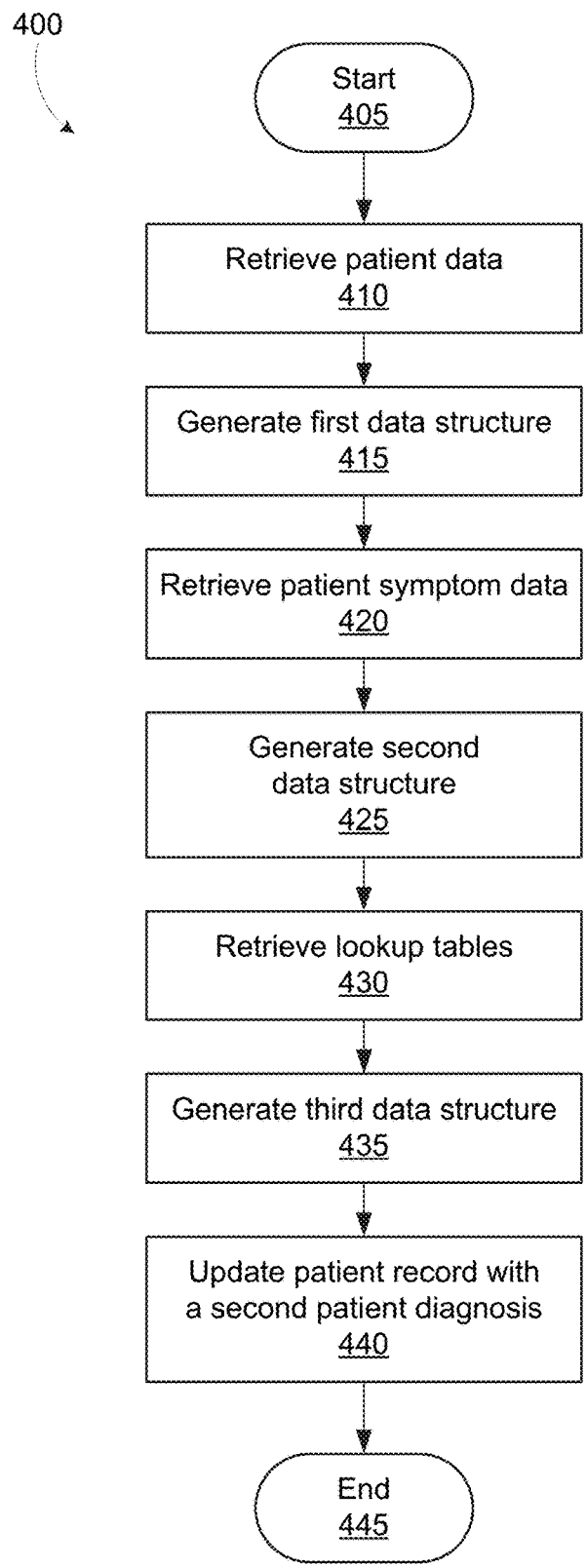
FIG. 4 is a flow diagram depicting an example method of detecting inaccuracies in comorbidity documentation, according to an illustrative implementation.

FIG. 4 is a flow diagram depicting an example method 400 of detecting inaccuracies in comorbidity documentation. The method 400 can begin (stage 405). The method 400 can include retrieving patient data (stage 410), generating a first data structure (stage 415), retrieving patient symptom data (stage 420), generating a second data structure (stage 425), retrieving lookup tables (stage 430), generating a third data structure (stage 435), updating a patient record with a second patient diagnosis (stage 440), and ending (stage 445).

The method 400 can include retrieving patient data (stage 410). The patient filter 120 can retrieve patient data from the hospital records database 160. The patient data can include data on all of the patients who visited or otherwise had a recorded interaction with the hospital over a time period of interest. The time period of interest can be the preceding day, the preceding week, the preceding year, or any other period of time up to and including the current admission. The patient data can include data for both patients who were admitted and patients who were not admitted.

The method 400 can include generating a first data structure (stage 415). The patient filter 120 can use the retrieved patient data to generate a first data structure representing a list of patient identifiers. Each patient identifier can correspond to an eligible patient having a through hospitalization for a specified time period. The patient filter 120 can determine whether a patient was admitted for a through hospitalization based on encounter-level data such as encounter type and encounter location. This process is discussed in more detail below with regard to FIG. 5. The first data structure can represent a list of patient identifiers corresponding to an eligible patient having a through hospitalization for a specified time period. The patient filter 120 can store the first data structure in the memory 145.

The method 400 can include retrieving patient symptom data (stage 420). The diagnosis aggregator 125 can retrieve patient symptom data and patient diagnosis data for each patient identifier listed in the first data structure. The diagnosis aggregator 125 can retrieve the patient symptom data from the professional records database 165, the hospital records database 160, and/or the clinical records database 155. The diagnosis aggregator 125 can use the retrieved patient symptom data to generate the second data structure.

The method 400 can include generating a second data structure (stage 425). The diagnosis aggregator 125 can assign the retrieved patient symptom data to the eligible patients represented in the first data structure. In some implementations, the second data structure can include all patient symptom data for a predetermined period of time up to and including the current admission. In some implementations, the second data structure can include an attribute column indicated whether each patient symptom in the patient symptom data was retrieved from the professional records database, the hospital records database, or the clinical records database. In some implementations, the diagnostic codes can comprise ICD-9 and ICD-10 codes. The diagnosis detection engine 130 can use the second data structure to generate the third data structure, which can include CC or MCC codes not previously recorded in the patient records.

The method 400 can include retrieving lookup tables 200, 230, and 260 (stage 430). The diagnosis detection engine 130 can use the lookup tables 200, 230, and 260 to generate the third data structure, which can include CC or MCC codes not previously recorded in the patient records. The diagnosis detection engine 130 can retrieve a plurality of lookup tables from the memory 145. The plurality of lookup tables can include a first data table 200, a second data table 230, and a third data table 260. The first table 200 can comprise diagnostic codes assigned to chronic condition categories. The second data table 230 can comprise a list of clinical discrete data corresponding to unambiguous indicators of each chronic condition. The third data table 260 can comprise diagnostic codes assigned to complication or comorbidity (CC) or major complication or comorbidity (MCC) values for each chronic condition category. These tables were described in detail above with regard to FIG. 2.

The method 400 can include generating a third data structure (stage 435). The diagnosis detection engine 130 can analyze the second data structure using the lookup tables 200, 230, and 260. The diagnosis detection engine 130 can apply the lookup tables 200, 230, and 260 to the second data structure. By applying the lookup tables 200, 230, and 260 to the second data structure, the diagnosis detection engine can assign a CC or a MCC value to at least one unique patient identifier of the second data structure. This process is described in more detail below with regard to FIG. 6. The diagnosis engine 130 can store the third data structure to the memory 145.

The method 400 can include updating a patient record with a second patient diagnosis (stage 440). The records updater 135 can update the hospital records database 160 with the CC or the MCC value assigned to at least one unique patient identifier represented in the third data structure The method 400 can end at stage 445.

Figure 5:
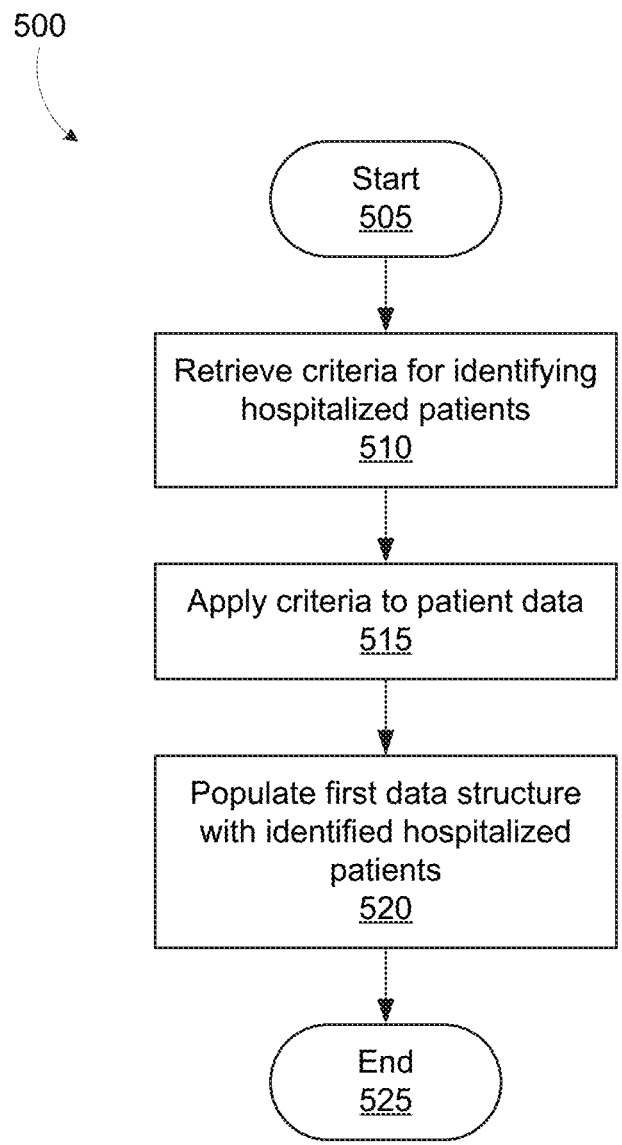
FIG. 5 is a flow diagram depicting an example method of generating a curated list of admitted patients, according to an illustrative implementation.

FIG. 5 is a flow diagram depicting an example method 500 of generating a curated list of admitted patients, according to an illustrative implementation. The method 500 can begin at stage 505. The method 500 can include retrieving criteria for identifying hospitalized patients (stage 510), applying the criteria to patient data (stage 515) and populating a first data structure with identified hospitalized patients (stage 520). The method 500 can end at stage 525.

The method 500 can include retrieving criteria for identifying hospitalized patients (stage 510). For example, the patient filter 120 can determine whether a patient was admitted based on encounter-level data such as encounter type and encounter location. The patient filter 120 can use the encounter location information to determine whether a patient visited an in-patient facility such as a hospital, or an out-patient facility such as a walk-in clinic. For example, a patient visit to an out-patient facility probably could not result in a hospital admission. The patient filter 120 can use the encounter type to determine whether a patient visit included out-patient services such as routine tests or imaging, or in-patient services such as major surgery. To make the determinations, the patient filter 120 can retrieve a set of criteria for identifying hospitalized patients in the patient data from the memory 145. The criteria can take the form of one or more lookup tables that the patient filter 120 can apply to the patient data to identify hospitalized patients. In some implementations, the lookup table can specify encounter types and encounter locations indicative of a patient hospitalization.

The method 500 can include applying the criteria to patient data (stage 515). The patient filter 120 can apply the set of criteria to the patient data to identify hospitalized patients. All patient visits matching the criteria in the lookup tables can be considered admitted patients for the purpose of this filtering. The method 500 can include populating a first data structure with identified hospitalized patients (stage 520). The patient filter 120 can perform, using the retrieved set of criteria, an extract, transform, load process on the patient data to populate the first data structure with the identified hospitalized patients. The method 500 can end at stage 525.

Figure 6:
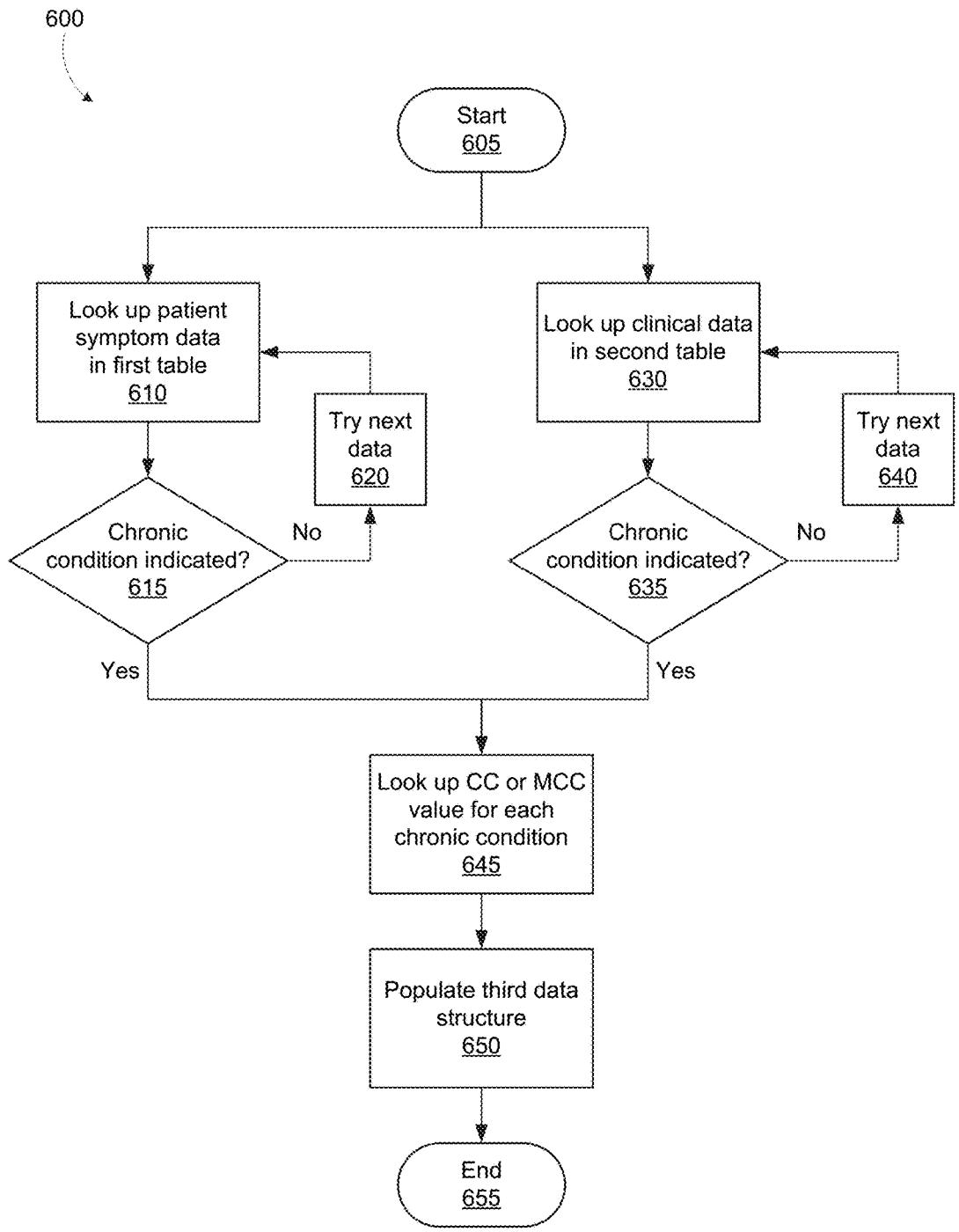
FIG. 6 is a flow diagram depicting an example method of assigning previously unrecorded CC and MCC values to patient records, according to an illustrative implementation.

FIG. 6 is a flow diagram depicting an example method 600 of assigning previously unrecorded CC and MCC values to patient records, according to an illustrative implementation. The method 600 can apply the lookup tables to the retrieved patient symptom data and clinical data to generate the third data structure. The method 600 can begin at stage 605. The method 600 can include looking up the patient symptom data in the first lookup table (stage 610), determining whether the diagnosis indicates a chronic condition (decision block 615), looking up the next diagnosis (stage 620), looking up the clinical data in the second lookup table (stage 630), determining whether the clinical data indicates a chronic condition (decision block 635), looking up the next clinical data (stage 640), looking up complication or comorbidity (CC) or major complication or comorbidity (MCC) values in the third lookup table for each chronic condition indicated (stage 645), and populating the third data structure with the CC and MCC values (stage 650). The method 600 can end at stage 655.

The method 600 can include looking up the patient symptom data in the first lookup table (stage 610). For each patient identifier in the second data structure, the diagnosis detection engine 130 can check each symptom or diagnosis associated with that patient identifier against the first lookup table 200. As described above with respect to FIG. 2, the first lookup table 200 can comprise diagnostic codes assigned to chronic condition categories. The method 600 can include determining whether the patient symptom data indicates a chronic condition in the first lookup table 200 (decision block 615). If the patient symptom data does not indicate a chronic condition, the method 600 can include looking up the next diagnosis (stage 620).

If the patient symptom data does indicate a chronic condition, the method 600 can include looking up CC or MCC values in the third lookup table 260 for the chronic condition indicated (stage 645). As described above with respect to FIG. 2, the third lookup table 260 can comprise diagnostic codes assigned to CC or MCC values for each chronic condition category. The method 600 can include and populating the third data structure with the CC and MCC values (stage 650). The third data structure can comprise an entity attribute table comprising columns for unique patients, condition, a CC or an MCC value, and a classification of whether the condition was present in one or more of the professional records database, the hospital records database, or the clinical records database.

The method 600 can include looking up the clinical data in the second lookup table (stage 630). For each patient identifier in the second data structure, the diagnosis detection engine 130 can check any clinical data associated with that patient identifier against the second lookup table 230. As described above with respect to FIG. 2, the second lookup table 230 can comprise a list of clinical discrete data corresponding to unambiguous indicators of each chronic condition. The method 600 can include determining whether the clinical data indicates a chronic condition in the second lookup table 230 (decision block 635). If the clinical data does not indicate a chronic condition, the method 600 can include looking up the next clinical data (stage 640).

If the clinical data does indicate a chronic condition, the method 600 can look up CC or MCC values in the third lookup table 260 for the chronic condition indicated (stage 645), and populate the third data structure with the CC and MCC values (stage 650). The method 600 can end at stage 655.

Figure 7:
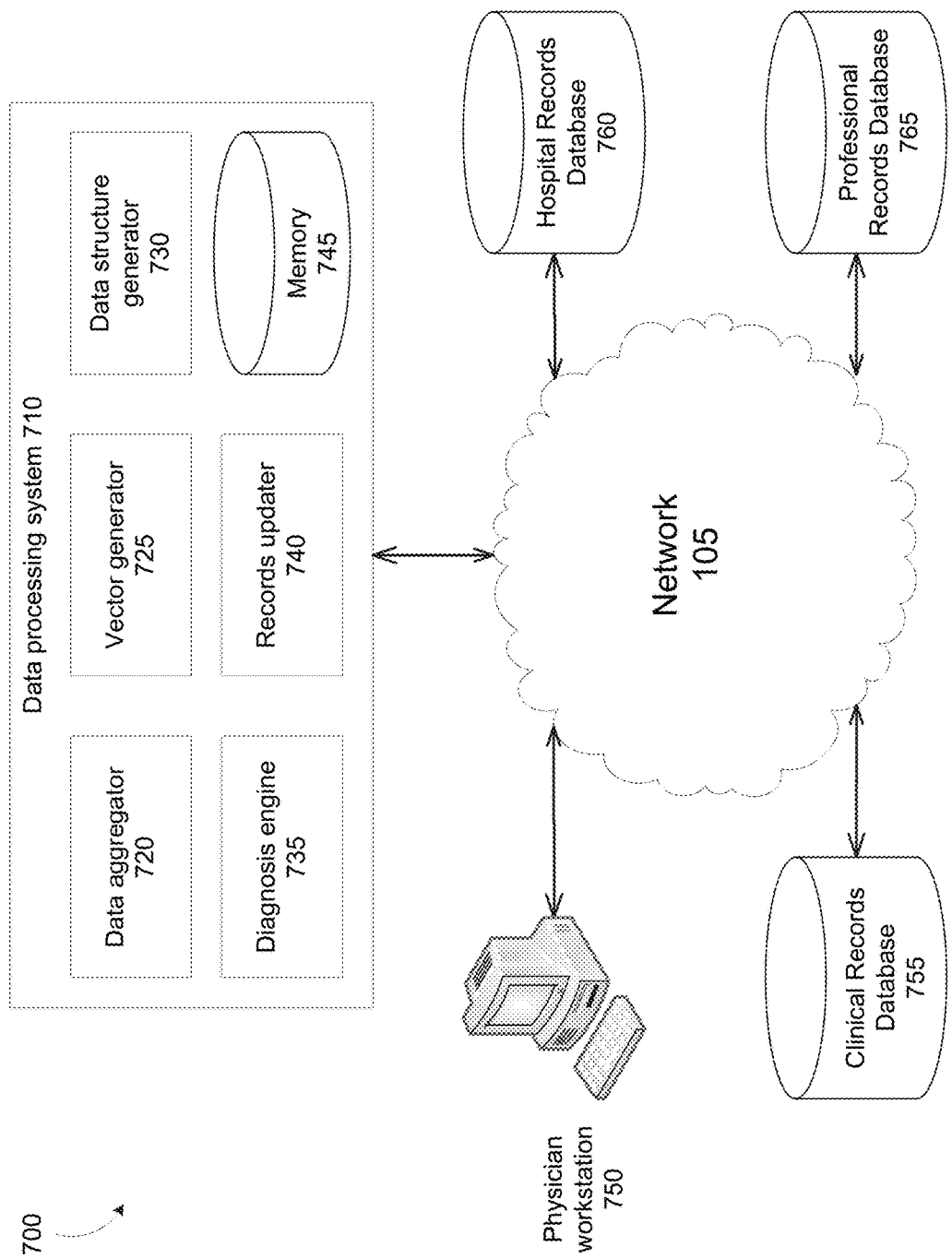
FIG. 7 is a block diagram illustrating an example environment for detecting inaccuracies in comorbidity documentation, according to another illustrative implementation.

FIG. 7 is a block diagram illustrating an example environment 700 for detecting inaccuracies in comorbidity documentation, according to another illustrative implementation. The environment 700 can include a data processing system 710, a physician workstation 750, a clinical records database 755, a hospital records database 760, and a professional records database 765, all communicatively connected via a computer network 105.

The physician workstation 750 can include a PC or PC-type computer used by a physician or healthcare worker to retrieve and enter healthcare data regarding a patient. In some implementations, the physician workstation 750 can be similar to the physician workstation 150 described above with respect to FIG. 1. The physician workstation 750 can connect to the clinical records database 755 via a secure, private computer network such as an internal hospital local area network ("LAN") or via a wider, unsecure computer network 105 such as the Internet. During a patient visit, the healthcare worker can retrieve a patient's medical record to the physician workstation 750 from the clinical records database 755. The healthcare worker can enter new medical information concerning the patient into the patient's medical record, and transmit it back to the clinical records database 755. The clinical records database 755 can store diagnoses of the patient in prose or in the form of diagnostic codes, such as those that conform to diagnosis-related groups ("DRG"). The clinical records database 755 can additionally include medical data such as the results of tests, screens, or imaging; for example, blood tests, urine screens, X-rays, or MRI images. The clinical records database 755 can store the patient's medical records, and make it available for future visits by the patient to the same or different medical facility.

The professional records database 765 can include records of all services performed by physicians, specialists, and other healthcare workers. In some implementations, the professional records database 765 can be similar to the professional records database 165 described above with respect to FIG. 1. Records for physician services can be separate from records for hospital services such as visits to the ER or other treatment centers, tests performed or treatments given, or medications or devices purchased at a pharmacy or store associated with the hospital. Records of hospital services can be stored in and retrieved from the hospital records database 760. In some implementations, the hospital records database 760 can be similar to the hospital records database 160 described above with respect to FIG. 1. Both the professional records database 765 and the hospital records database 760 can be connected to the network 105.

The data processing system 710 can perform the operations for detecting comorbidity in patient data. The data processing system 710 can include a data aggregator 720, a vector generator 725, a data structure generator 730, a diagnosis engine 735, a records updater 740, and a memory 745. In some implementations, the memory 745 can be similar to the memory 145 described above with respect to FIG. 1. The data processing system 710 can retrieve data from the clinical records database 755, the hospital records database 760, and the professional records database 765 via the network 105.

The data aggregator 720 can be configured to retrieve, from the clinical records database 755, a patient record including a first patient diagnosis having a first diagnosis code. The data aggregator 720 can be configured to retrieve, from the hospital records database 760, patient symptom data. In some implementations, the data aggregator 720 can retrieve additional patient symptom data from the hospital records database 760 or the professional records database 765.

The vector generator 725 can be configured to generate a vector from the patient symptom data. In embodiments where the data aggregator 720 can be configured to retrieve additional patient symptom data from the hospital records database 760 and the professional records database 765, the vector generator 725 can generate the vector using the patient symptom data and the additional patient symptom data, or a second vector using the additional patient symptom data.

The data structure generator 730 can be configured to generate a data structure comprising a plurality of diagnoses, each diagnosis of the plurality of diagnoses including a plurality of symptom states. In some implementations, the data structure generator 720 can generate the data structure in the form of a table having a plurality of columns and a plurality of rows. Each column of the plurality of columns can represent one of the plurality of diagnoses, and each row of the plurality of rows can represent one of a plurality of symptoms. Each element of the table can represent a value of a symptom state for a diagnosis of the corresponding column. An example data structure 850 is described below with reference to FIG. 8.

The diagnosis engine 735 can be configured to detect signals indicating a diagnosis. In some implementations, the diagnosis engine 735 can be similar to the diagnosis detection engine 130 described above with respect to FIG. 1. The diagnosis engine 735 can be configured to compare the vector to each diagnosis in the data structure, and determine that the vector matches a diagnosis in the data structure. In some embodiments, the diagnosis engine 735 can compare the vector to the data structure by comparing each element of the vector to a corresponding element in each column of the data structure. In some embodiments, the diagnosis engine 735 can determine that the vector matches the diagnosis by determining that a correlation between each element of the vector and the corresponding element of the column corresponding to the diagnosis exceeds a predetermined threshold. In some embodiments, the diagnosis engine 735 can determine that the vector matches the diagnosis by determining that each element of the vector matches each corresponding element of the column corresponding to the diagnosis.

The records updater 740 can be configured to update the patient record with a second patient diagnosis having a second diagnosis code that includes a comorbidity designation. In some implementations, the records updater 740 can be similar to the records updater 135 described above with respect to FIG. 1. In some embodiments, the diagnosis codes can conform to a diagnosis-related group. In some embodiments, the comorbidity designation can include one of a complication or comorbidity or a major complication or comorbidity designation.

FIG. 8 is an illustration of an example vector 800 and an example data structure 850 for use in detecting inaccuracies in comorbidity documentation. The vector 800 can be an array of element values representing symptom states extracted from patient data. The vector 800 can have any number of rows or columns. In some embodiments, the vector 800 can be a one-dimensional array having a column 805 and a plurality of rows 810a-810x. Each row 810a-810c can correspond to a symptom; for example, body mass index, vital sign data such as blood pressure, clinical lab values such as cholesterol, or medication. The total number of elements 815a-815x can depend on the number of possible different symptoms that the system can analyze. Each element of the vector 800 can contain a value 815 corresponding to a discrete symptom state; for example, the presence or measures of body mass index, vital sign data such as blood pressure, clinical lab values such as cholesterol, or medication. The value 815 can be Boolean (i.e., indicating the presence or absence of a symptom state), a qualitative measure of a symptom state (e.g., mild, moderate, or severe), or a quantitative measure of a symptom state (e.g., blood pressure or cholesterol level).

The data structure 850 can be an array of values representing expected or typical symptom states for different diagnoses. The data structure 850 can have any number of rows or columns. In some embodiments, the data structure 850 can be a two-dimensional array having a plurality of columns 855a-855c and a plurality of rows 860a-860z. Each column 855a-855c can correspond to a diagnosis; for example, cancer, high cholesterol, obesity, malnutrition, hypertension, chronic kidney disease, etc. Each row 860a-860z can correspond to a symptom; for example, body mass index, vital sign data such as blood pressure, clinical lab values such as cholesterol, or medication. Each element of the data structure 850 can contain values—for example, 865a-865z, 870a-870z, and 875a-875z—corresponding to an expected or typical value for a symptom state. Values for symptom states can include, for example, ranges of expected body mass index, blood pressure, and cholesterol levels.

Figure 9:
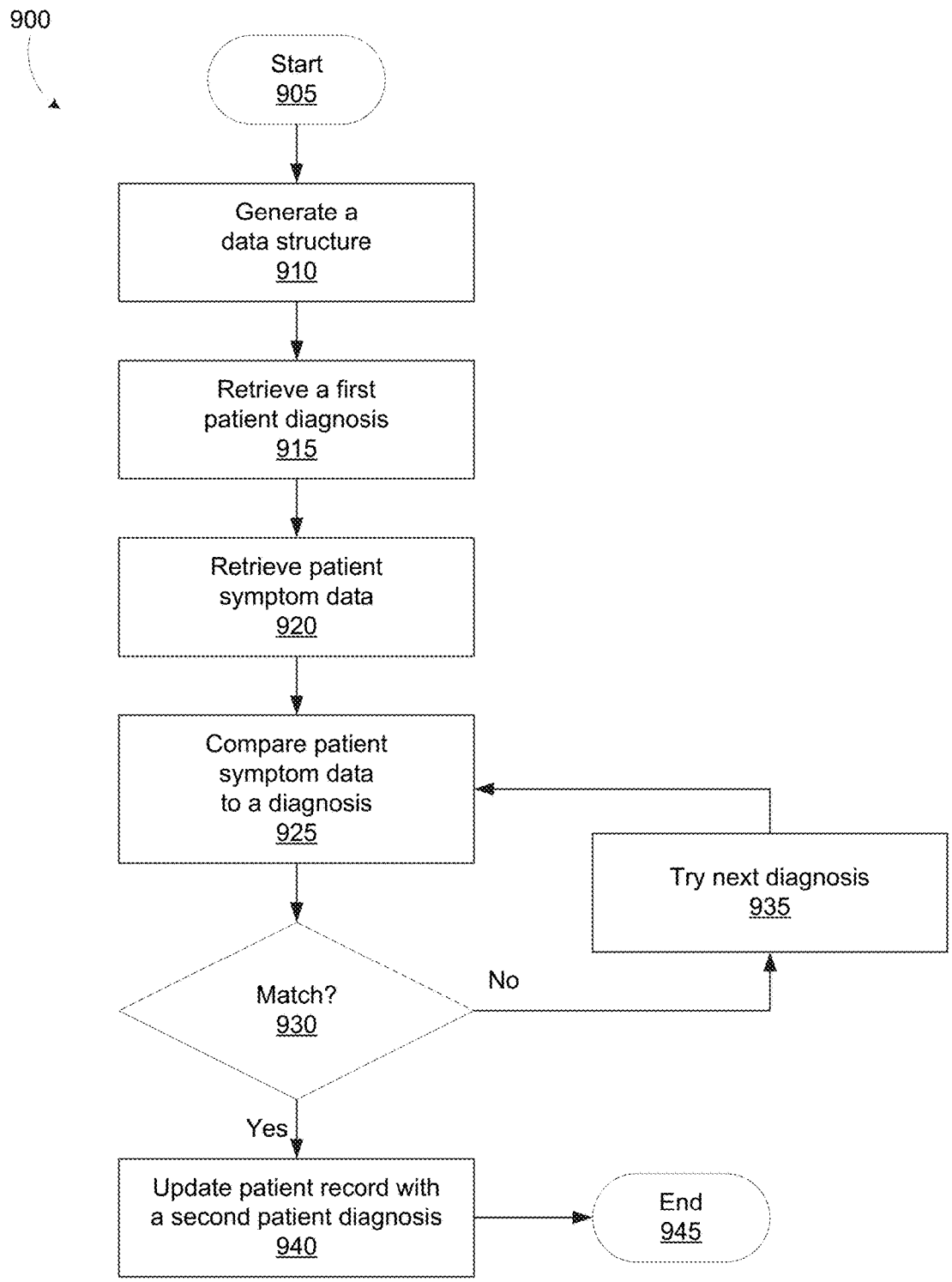
FIG. 9 is a flow diagram depicting an example method for detecting inaccuracies in comorbidity documentation, according to another illustrative implementation.

FIG. 9 is a flow diagram depicting an example method 900 for detecting inaccuracies in comorbidity documentation. The method 900 can start with stage 905. The method 900 can include generating a data structure (stage 910), retrieving a first patient diagnosis (stage 915), retrieving patient symptom data (stage 920), comparing patient symptom data to a diagnosis (stage 925), and determining whether the patient symptom data matches a diagnosis (decision block 930). If the method 900 determines (at decision block 930) that the patient symptom data does not match a diagnosis, the method 900 can include trying the next diagnosis (stage 935) and repeating stage 925 and decision block 930. If the method 900 determines (at decision block 930) that the patient symptom data matches a diagnosis, the method 900 can include updating the patient record with a second patient diagnosis (stage 940). The method 900 can end with stage 945.

The method 900 can include generating a data structure (stage 910). The data structure 850 can include a plurality of diagnoses, each diagnosis of the plurality of diagnoses including a plurality of symptom states. The data structure generator 730 can generate the data structure 850 by generating a table with a plurality of columns and a plurality of rows, each column of the plurality of columns representing one of the plurality of diagnoses, and each row of the plurality of rows representing one of a plurality of symptoms, such that each element of the table represents a value of a symptom state for a diagnosis of the corresponding column.

The method 900 can include retrieving a first patient diagnosis (stage 915). The data aggregator 720 can retrieve, from the clinical records database 755, a patient record including a first patient diagnosis having a first diagnosis code.

The method 900 can include retrieving patient symptom data (stage 920). The data aggregator 720 can retrieve patient symptom data from a hospital records database 760. The data aggregator 720 can generate a vector 800 from the patient symptom data.

The method 900 can include comparing patient symptom data to a diagnosis (stage 925). The diagnosis engine 735 can compare the vector 800 to each diagnosis in the data structure 850. In some embodiments, the method 900 can include comparing the vector 800 to the data structure 850 by comparing each element of the vector 850 to a corresponding element in each column of the data structure.

The method 900 can include determining whether the patient symptom data matches a diagnosis (decision block 930). The diagnosis engine 735 can determine that the vector 800 matches a diagnosis in the data structure 850. In some embodiments, the method 900 can determine that the vector 800 matches the diagnosis by determining that a correlation between each element of the vector 800 and the corresponding element of the column 855 corresponding to the diagnosis exceeds a predetermined threshold. In some embodiments, the predetermined threshold can be different for different diagnoses. In other words, each possible diagnosis may require a different level confidence for confirming the diagnosis. Such a threshold can be recorded as an additional element in the column; for example, as the element 865y for the diagnosis corresponding to the column 855a. In some embodiments, the method 900 can determine that the vector 800 matches the diagnosis by determining that each element of the vector each corresponding element of the column corresponding to the diagnosis.

If the method 900 determines (at decision block 930) that the patient symptom data matches a diagnosis, the method 900 can include updating the patient record with a second patient diagnosis (stage 940). The records updater 740 can update the patient record with a second patient diagnosis having a second diagnosis code that includes a comorbidity designation.

If the method 900 determines (at decision block 930) that the patient symptom data does not match that diagnosis, the method 900 can include trying the next diagnosis (stage 935) and repeat stage 925 and decision block 930. If the patient symptom data does not match any diagnosis in the data structure 850, than the method 900 can end (stage 945) without updating the patient record.

In some embodiments, certain acts of the method 900 can be repeated for additional patient symptom data retrieved from the professional records database 765. The vector generator 725 can generate the vector 800 from the first patient symptom data and the additional patient symptom data.

In some embodiments, the method 900 can include retrieving data retrieved from the professional records database 765, and generating a second vector from the additional patient symptom data. The vector generator 725 can generate a second vector from the additional patient symptom data retrieved from the professional records database 765. The diagnosis engine 735 can determine that the second vector matches a second diagnosis in the data structure 850. The records updater 740 can, based on the determination, update the patient record with a third patient diagnosis having a third diagnosis code that includes a second comorbidity designation.

Figure 10:
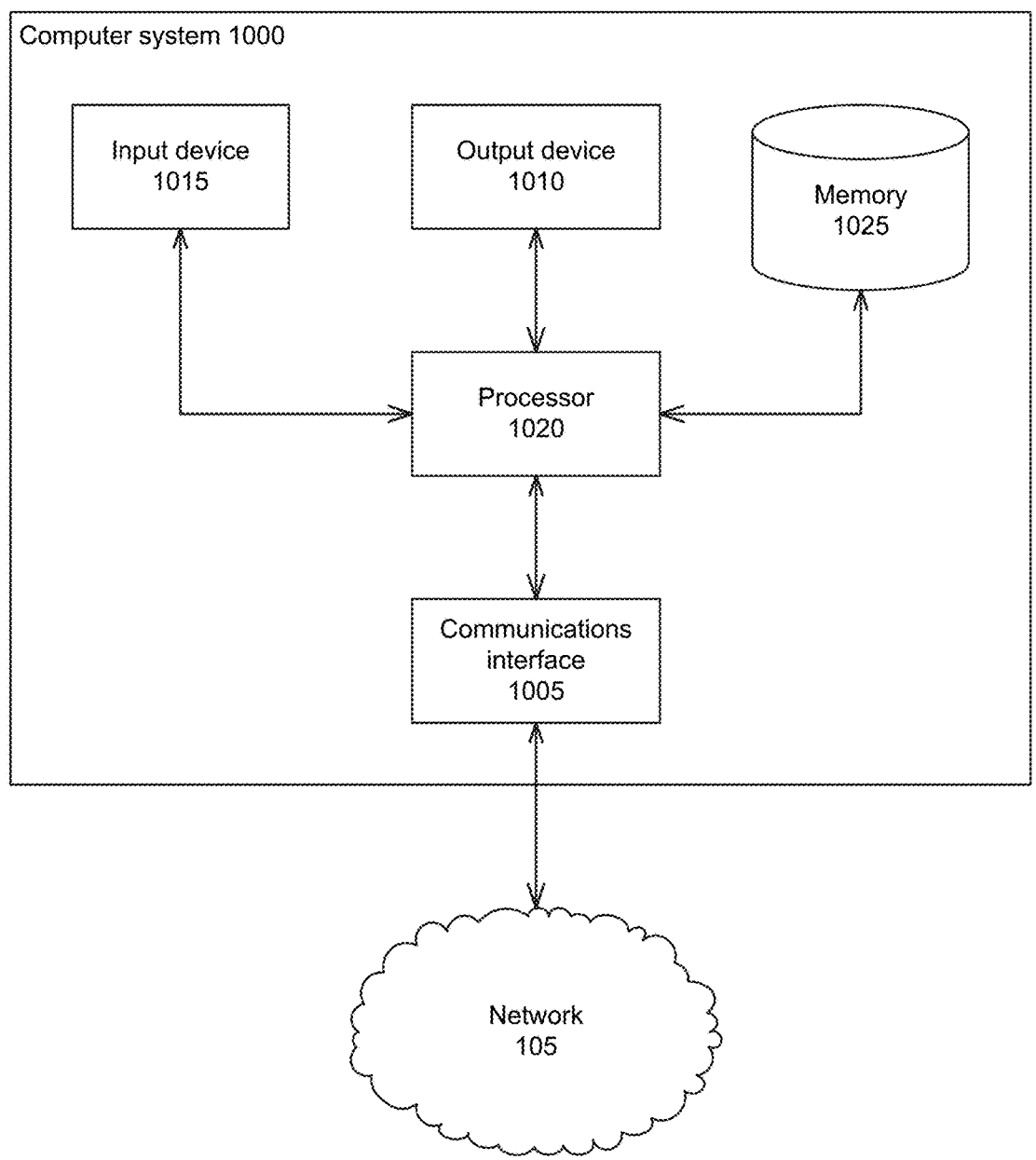
FIG. 10 is a block diagram of an example computer system that may implement elements of the systems and methods described herein.

FIG. 10 is a block diagram of an example computer system 1000 that may implement elements of the systems and methods described herein (including the data processing system 110, the data processing system 710, and their respective components) in accordance with some embodiments. The computer system 1000 can be used to receive and provide information via the network 105; for example, to detect inaccuracies in comorbidity documentation. The computer system 1000 can include one or more processors 1020 communicatively coupled to at least one memory 1025, one or more communications interfaces 1005, one or more output devices 1010 (e.g., one or more display units) or one or more input devices 1015 (e.g., one or more keyboards, mice, touchscreens, keypads, microphones, or the like). The processors 1020 can be included in the data processing system 110.

The memory 1025 can include non-transitory computer-readable storage media, and can store computer instructions such as processor-executable instructions for implementing the operations described herein. The data processing system 110, or components of thereof, can include the memory 1025 to store the data retrieved from the clinical records database 155, the hospital records database 160, or the professional records database 155, for example. The at least one processor 1020 can execute instructions stored in the memory 1025 and can read from or write to the memory information processed and or generated pursuant to execution of the instructions.

The processors 1020 can be communicatively coupled to or control the at least one communications interface 1005 to transmit or receive information pursuant to execution of instructions. For example, the communications interface 1005 can be coupled to a wired or wireless network, bus, or other communication means and can allow the computer system 1000 to transmit information to or receive information from other devices (e.g., other computer systems). One or more communications interfaces 1005 can facilitate information flow between the components of the environment 100. In some embodiments, the communications interface 1005 can (e.g., via hardware components or software components) provide a website as an access portal to at least some aspects of the computer system 1000. Examples of communications interfaces 1005 include modems, network adapters, and user interfaces.

The output device 1010 can allow information to be viewed or perceived in connection with execution of the instructions. The output device 1010 can include, for example and without limitation, a display monitor, projector, audio interface, or printer. The input device 1015 can allow a user to make manual adjustments, make selections, enter data or other information, or interact in any of a variety of manners with the processor during execution of the instructions. The input device 1015 can include, for example and without limitation, a keyboard, mouse, touchscreen, or microphone.

The subject matter and the operations described herein can be implemented in digital electronic circuitry, or in computer software, firmware, or hardware, including the structures disclosed in this specification and their structural equivalents, or in combinations of one or more of them. The subject matter described in this specification can be implemented as one or more computer programs; for example, one or more modules of computer program instructions, encoded on computer storage medium for execution by, or to control the operation of, data processing apparatus. The program instructions can be encoded on an artificially generated propagated signal; for example, a machine-generated electrical, optical, or electromagnetic signal that is generated to encode information for transmission to suitable receiver apparatus for execution by a data processing system or apparatus. A computer storage medium can be, or be included in, a computer-readable storage device, a computer-readable storage substrate, a random or serial access memory array or device, or a combination of one or more of them. While a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "data processing system" or "computing device" "module" "engine" or "component" encompasses apparatus for processing data including, without limitation, a programmable processor, a computer, a system on a chip, or combinations thereof. The apparatus can include special purpose logic circuitry; for example, a field programmable gate array (FPGA) or application specific integrated circuit (ASIC). The apparatus can also include code that can create an execution environment for the computer program in question. The apparatus and execution environment can realize various different computing model infrastructures, such as web services, distributed computing, and grid computing infrastructures. The data processing system 110 or the components thereof can include or share one or more data processing apparatus, systems, computing devices, or processors.

While operations are depicted in the drawings in a particular order, the operations are not required to be performed in the particular order shown or in sequential order, and all illustrated operations are not required to be performed. Actions described herein can be performed in a different order.

The separation of various system components does not require separation in all embodiments, and the described program components can be included in a single hardware or software product. For example, the patient filter 120, the diagnosis aggregator 125, the diagnosis detection engine 130, and the records updater 135 can be a single module, a logic device having one or more processing circuits, or part of one or more servers of the data processing system 110. The same can hold true for the components of the data processing system 710.

Having now described some illustrative embodiments, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one embodiments are not intended to be excluded from a similar role in other embodiments or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate embodiments consisting of the items listed thereafter exclusively. In one embodiment, the systems and methods described herein consist of one, each combination of more than one, or all of the described elements, acts, or components.

Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements to single or plural configurations. References to any act or element being based on any information, act or element may include embodiments where the act or element is based at least in part on any information, act, or element.

Any embodiment disclosed herein may be combined with any other embodiment or embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one implementation or embodiment. Such terms as used herein are not necessarily all referring to the same embodiment. Any embodiment may be combined with any other embodiment, inclusively or exclusively, in any manner consistent with the aspects and embodiments disclosed herein.

References to "or" may be construed as inclusive so that any terms described using "or" may indicate any of a single, more than one, and all of the described terms.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing embodiments are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A system for revising a benchmarked quality score of a hospital based on detecting inaccuracies in comorbidity documentation, comprising a memory and a processor configured to:
   retrieve patient data from a hospital records database;
   generate a first data structure representing a list of patient identifiers, each corresponding to an eligible patient being admitted to a hospital during a specified time period;
   retrieve patient symptom data for each patient identifier listed in the first data structure from one or more of a professional records database, a hospital records database, or a clinical records database;

generate a second data structure by assigning the retrieved patient symptom data to the eligible patients represented in the first data structure;
retrieve, from the memory, a plurality of lookup tables, the plurality of lookup tables comprising:
  a first table, comprising diagnostic codes assigned to chronic conditions,
  a second table, comprising a list of clinical discrete data corresponding to unambiguous indicators of each chronic condition, and
  a third table, comprising diagnostic codes assigned to complication or comorbidity (CC) or major complication or comorbidity (MCC) values for each chronic condition;
generate a third data structure by analyzing the retrieved patient symptom data by applying the plurality of lookup tables to the second data structure;
generate a first benchmarked quality score for each patient record by analyzing the third data structure against a plurality of quality measures for each chronic condition from a payer for medical services;
notify a healthcare provider of a second benchmarked quality score of the hospital generated by aggregation of the first benchmarked quality scores corresponding to patient records for all eligible patients being admitted to a hospital during a specified time period;
determine whether there is presence of any unrecorded CC or MCC values to patient record;
in response to the determination that there is unrecorded CC or MCC values to patient record, perform at least one of:
  look up the retrieved patient symptom data in the first table, determine whether the diagnostic code indicates a chronic condition, and when it is determined that the diagnostic code does not indicate a chronic condition, look at next patient symptom data, or
  look up clinical discrete data in the second table, determine whether the clinical discrete data indicates a chronic condition, and
  when it is determined that the clinical discrete data does not indicate a chronic condition, look at next clinical discrete data, and when it is determined that the chronic condition is indicated, look up CC or MCC values in the third table for the indicated chronic condition;
assign the CC or a MCC value to at least one unique patient identifier of the third data structure, wherein the third data structure contains fields for the at least one unique patient identifiers, chronic conditions, CC or MCC values, and classifications of whether each chronic condition was present in one or more of the professional records database, the hospital records database, or the clinical records database;
store the CC or the MCC value assigned to the at least one unique patient identifier to the third data structure to the memory;
update the hospital records database with an indication of the CC or the MCC value assigned to the at least one unique patient identifiers;
generate a third benchmarked quality score for each patient record by analyzing the third data structure in response to assignment of the CC or the MCC value to the at least one unique patient identifiers against the plurality of quality measures for each chronic condition from the payer for medical services; and
notify a healthcare provider of a fourth benchmarked quality score of the hospital generated by aggregation of the third benchmarked quality scores corresponding to patient records for all eligible patients being admitted to a hospital during a specified time period.

2. The system of claim 1, wherein the system generates the first data structure by:
  retrieving a set of criteria for identifying hospitalized patients in the patient data;
  applying the set of criteria to the patient data to identify hospitalized patients; and
  performing, using the retrieved set of criteria, an extract, transform, load process on the patient data to populate the first data structure with the identified hospitalized patients.

3. The system of claim 2, wherein the set of criteria comprises a lookup table specifying encounter types and encounter locations indicative of a patient hospitalization.

4. The system of claim 1, wherein the second data structure includes all patient symptom data for a predetermined period of time up to and including current admission.

5. The system of claim 4, wherein the second data structure includes an attribute column indicating whether each patient symptom in the patient symptom data was retrieved from the professional records database, the hospital records database, or the clinical records database.

6. The system of claim 1, wherein the diagnostic codes comprise ICD-9 and ICD-10 codes.

7. The system of claim 1, wherein the chronic conditions comprise cancer, major depression, epilepsy, ischemic heart disease, osteoporosis, chronic obstructive pulmonary disease, osteoarthritis, dementia, cerebrovascular disease, asthma, bipolar disorder, high cholesterol, obesity, malnutrition, hypertension, chronic kidney disease, congestive heart failure, diabetes mellitus, hyponatremia, hypernatremia, and acute renal failure.

8. The system of claim 1, wherein the list of clinical discrete data comprises one or more of lab results, vital signs, or medication data that unambiguously indicate presence of a medical diagnosis.

9. The system of claim 1, wherein the third data structure is an entity attribute table.

10. The system of claim 1, wherein a CC or a MCC value is assigned to at least one unique patient identifier of the second data structure upon determining the CC or the MCC is applicable to the benchmarked quality score of the hospital.

11. A method, executed by a data processing system having a memory and a processor, of detecting inaccuracies in comorbidity documentation, comprising:
  retrieving, by the data processing system, patient data from a hospital records database;
  generating, by the processor, a first data structure representing a list of patient identifiers, each corresponding to an eligible patient being admitted to a hospital during a specified time period;
  retrieving patient symptom data for each patient identifier listed in the first data structure from one or more of a professional records database, a hospital records database, or a clinical records database;
  generating, by the processor, a second data structure by assigning the retrieved patient symptom data to the eligible patients represented in the first data structure;
  retrieving, from the memory, a plurality of lookup tables, the plurality of lookup tables comprising:
    a first table, comprising diagnostic codes assigned to chronic conditions, a second table, comprising a list of clinical discrete data corresponding to unambiguous indicators of each chronic condition, and a third table, comprising diagnostic codes assigned to complication or comorbidity (CC) or major complication or comorbidity (MCC) values for each chronic condition;

generating, by the processor, a third data structure by analyzing the retrieved patient symptom data by applying the plurality of lookup tables to the second data structure;

generating, by the processor, a first benchmarked quality score for each patient record by analyzing the third data structure against a plurality of quality measures for each chronic condition from a payer for medical services;

notifying a healthcare provider of a second benchmarked quality score of the hospital generated by aggregation of the first benchmarked quality scores corresponding to patient records for all eligible patients being admitted to a hospital during a specified time period;

determining whether there is presence of any unrecorded CC or MCC values to patient record;

in response to the determination that there is unrecorded CC or MCC values to patient record, performing at least one of:

looking up the retrieved patient symptom data in the first table, determine whether the diagnostic code indicates a chronic condition, and when it is determined that the diagnostic code does not indicate a chronic condition, look at next patient symptom data, or looking up clinical discrete data in the second table, determine whether the clinical discrete data indicates a chronic condition, and when it is determined that the clinical discrete data does not indicate a chronic condition, looking at next clinical discrete data, and when it is determined that the chronic condition is indicated, looking up CC or MCC values in the third table for the indicated chronic condition;

assigning the CC or a MCC value to at least one unique patient identifier of the second data structure, wherein the third data structure includes fields for at least one unique patient identifiers, chronic conditions, CC or MCC values, and classifications of whether each chronic condition was present in one or more of the professional records database, the hospital records database, or the clinical records database;

storing the CC or the MCC value assigned to the at least one unique patient identifier to the third data structure to the memory;

updating the hospital records database with an indication of the CC or the MCC value assigned to the at least one unique patient identifiers; and generating, by the processor, a third benchmarked quality score for each patient record by analyzing the third data structure in response to assignment of the CC or the MCC value to the at least one unique patient identifiers against the plurality of quality measures for each chronic condition from the payer for medical services; and notifying a healthcare provider of a fourth benchmarked quality score of the hospital generated by aggregation of the third benchmarked quality scores corresponding to patient records for all eligible patients being admitted to a hospital during a specified time period.

12. The method of claim 11, further comprising:
generating the first data structure by:
retrieving a set of criteria for identifying hospitalized patients in the patient data;
applying the set of criteria to the patient data to identify hospitalized patients; and
performing, using the retrieved set of criteria, an extract, transform, load process on the patient data to populate the first data structure with the identified hospitalized patients.

13. The method of claim 12, wherein the set of criteria comprises a lookup table specifying encounter types and encounter locations indicative of a patient hospitalization.

14. The method of claim 11, wherein the second data structure includes all patient symptom data for a predetermined period of time up to and including current admission.

15. The method of claim 14, wherein the second data structure includes an attribute column indicating whether each patient symptom in the patient symptom data was retrieved from the professional records database, the hospital records database, or the clinical records database.

16. The method of claim 11, wherein the diagnostic codes comprise ICD-9 and ICD-10 codes.

17. The method of claim 11, wherein the chronic conditions comprise cancer, major depression, epilepsy, ischemic heart disease, osteoporosis, chronic obstructive pulmonary disease, osteoarthritis, dementia, cerebrovascular disease, asthma, bipolar disorder, high cholesterol, obesity, malnutrition, hypertension, chronic kidney disease, congestive heart failure, diabetes mellitus, hyponatremia, hypernatremia, and acute renal failure.

18. The method of claim 11, wherein the list of clinical discrete data comprises one or more of lab results, vital signs, or medication data that unambiguously indicate presence of a medical diagnosis.

19. The method of claim 11, wherein the third data structure is an entity attribute table.

20. The method of claim 11, wherein a CC or a MCC value is assigned to at least one unique patient identifier of the second data structure upon determining the CC or the MCC is applicable to the benchmarked quality score of the hospital.

* * * * *